US011504253B2

(12) United States Patent
Ryan et al.

(10) Patent No.: US 11,504,253 B2
(45) Date of Patent: Nov. 22, 2022

(54) PULL WIRE FOR VASCULAR INTERVENTION DEVICE DELIVERY SYSTEM

(71) Applicant: Cook Medical Technologies LLC, Bloomington, IN (US)

(72) Inventors: Olivia Ryan, County Clare (IE); James Butler, County Tipperary (IE); Joe Hayes, County Clare (IE); Sean Cummins, County Limerick (IE)

(73) Assignee: Cook Medical Technologies LLC, Bloomington, IN (US)

( * ) Notice: Subject to any disclaimer, the term of this patent is extended or adjusted under 35 U.S.C. 154(b) by 162 days.

(21) Appl. No.: 16/413,132

(22) Filed: May 15, 2019

(65) Prior Publication Data
US 2019/0262154 A1 Aug. 29, 2019

Related U.S. Application Data

(63) Continuation of application No. 14/852,895, filed on Sep. 14, 2015, now Pat. No. 10,327,927.
(Continued)

(51) Int. Cl.
*A61F 2/95* (2013.01)
*A61F 2/962* (2013.01)
(Continued)

(52) U.S. Cl.
CPC ............... *A61F 2/95* (2013.01); *A61F 2/844* (2013.01); *A61F 2/962* (2013.01); *A61F 2/966* (2013.01);
(Continued)

(58) Field of Classification Search
CPC .. A61F 2/95; A61F 2/962; A61F 2/966; A61F 2/2427; A61F 2/2436;
(Continued)

(56) References Cited

U.S. PATENT DOCUMENTS 6,190,360 B1   2/2001   Iancea et al.
6,238,402 B1   5/2001   Sullivan, III et al.
(Continued)

FOREIGN PATENT DOCUMENTS

EP   2431009      3/2012
WO   2008034793   3/2008

OTHER PUBLICATIONS

Information Disclosure Statement and Declaration of Darach McGrath Re: ev3 Inc. Stent Delivery System On-Sale Jul. 11, 2013 Prior Art.

*Primary Examiner* — Erich G Herbermann
(74) *Attorney, Agent, or Firm* — Liell & McNeil (57) ABSTRACT

A vascular intervention device delivery system includes a catheter with a proximal end attached to a handle, and a distal carrier segment for mounting a vascular intervention device thereon. A retractable sheath is movable from a first position covering the distal carrier segment to a second position retracted proximally uncovering the distal carrier segment. A pull is attached to the retractable sheath and extends proximally from the retractable sheath toward the handle. A majority of the length of the pull has a cross sectional shape with a concave side that faces the longitudinal axis and is opposite to a convex side that faces away from the longitudinal axis. The cross sectional shape has a width that is greater than a thickness.

4 Claims, 5 Drawing Sheets

Related U.S. Application Data (60) Provisional application No. 62/050,388, filed on Sep. 15, 2014.

(51) Int. Cl.
    *A61F 2/844* (2013.01)
    *A61F 2/966* (2013.01)
    *A61B 17/00* (2006.01)

(52) U.S. Cl.
    CPC ... *A61B 2017/00407* (2013.01); *A61F 2/9517* (2020.05); *A61F 2230/0069* (2013.01)

(58) Field of Classification Search
    CPC ...... A61F 2/2439; A61F 2/844; A61F 2/9517; A61F 2002/9665; A61F 2230/0069; A61B 2017/00407
    See application file for complete search history.

(56) References Cited

U.S. PATENT DOCUMENTS

| | | | |
|---|---|---|---|
| 7,967,829 | B2 | 6/2011 | Gunderson et al. |
| 7,976,574 | B2 | 7/2011 | Papp |
| 8,500,789 | B2 | 8/2013 | Wuebbeling et al. |
| 2002/0103525 | A1 | 8/2002 | Cummings |
| 2003/0171642 | A1 | 9/2003 | Schock |
| 2004/0143272 | A1 | 7/2004 | Cully et al. |
| 2005/0038493 | A1* | 2/2005 | Feeser ............... A61F 2/966 623/1.11 |
| 2005/0149159 | A1 | 7/2005 | Andreas et al. |
| 2005/0273151 | A1 | 12/2005 | Fulkerson et al. |
| 2006/0259124 | A1 | 11/2006 | Matsuoka et al. |
| 2007/0032860 | A1 | 2/2007 | Brooks et al. |
| 2007/0055342 | A1 | 3/2007 | Wu et al. |
| 2007/0088421 | A1 | 4/2007 | Loewen |
| 2007/0156225 | A1 | 7/2007 | George et al. |
| 2007/0168014 | A1 | 7/2007 | Jimenez et al. |
| 2008/0091257 | A1 | 4/2008 | Andreas et al. |
| 2008/0167628 | A1 | 7/2008 | Li |
| 2009/0204197 | A1* | 8/2009 | Dorn ............... A61F 2/95 623/1.11 |
| 2009/0210046 | A1 | 8/2009 | Shumer et al. |
| 2010/0004606 | A1 | 1/2010 | Hansen et al. |
| 2012/0041537 | A1 | 2/2012 | Parker et al. |
| 2012/0059448 | A1 | 3/2012 | Parker et al. |
| 2012/0101562 | A1 | 4/2012 | Gunderson et al. |
| 2012/0116493 | A1 | 5/2012 | Harada |
| 2012/0123516 | A1 | 5/2012 | Gerdts et al. |
| 2012/0158120 | A1 | 6/2012 | Hacker et al. |
| 2012/0172915 | A1* | 7/2012 | Fifer ............... A61B 17/22031 606/200 |
| 2012/0330401 | A1 | 12/2012 | Sugimoto et al. |
| 2013/0013047 | A1 | 1/2013 | Ramos et al. |
| 2013/0018451 | A1 | 1/2013 | Grabowski et al. |
| 2013/0030522 | A1 | 1/2013 | Rowe et al. |
| 2013/0110223 | A1 | 5/2013 | Munsinger et al. |
| 2014/0188209 | A1 | 7/2014 | Loewen |
| 2015/0297378 | A1* | 10/2015 | Senness ............... A61F 2/966 623/1.11 |

* cited by examiner

PULL WIRE FOR VASCULAR INTERVENTION DEVICE DELIVERY SYSTEM

TECHNICAL FIELD

The present disclosure relates generally to vascular intervention device delivery systems, and more particularly to a curved cross-section pull wire for actuating deployment of a vascular intervention device.

BACKGROUND

Self expanding stents and similar vascular intervention devices are often delivered and deployed using so called pin and pull systems. Typically, the stent is compressed between a retractable outer sheath and an inner catheter. To deploy the stent, the user has to pull the outer sheath to uncover the stent using one hand while resisting the force with the other hand on the inner catheter to maintain the position of the stent during deployment. In pin and pull systems, the user can have difficultly maintaining the inner catheter at a fixed position while simultaneously moving the outer sheath. In very difficult stent deployments, which require a large amount of force by the user, this simultaneous push and pull may lead to inaccurate stent positioning, shortening or lengthening of the stent, or possibly even damage to the stent or target vessel. Another disadvantage of pin and pull systems is that there can be a lack of control on the deployment because the force to deploy the stent decreases as more of the stent is deployed. If the user maintains the same high force during deployment, the stent may be deployed too fast for the user to control. Another potential problem relates to building up tension in the outer sheath prior to movements thereof during the deployment process. If the user pauses during the deployment and releases this built up tension, deployment errors can occur when the user resumes tension to again move the outer sheath to the deployment position fully uncovering the self explaining stent. Another occasional problem relates to early partial deployment of a stent due to friction on the retractable sheath enroute to a delivery site.

The present disclosure is directed toward one or more of the problems set forth above.

SUMMARY OF THE DISCLOSURE

In one aspect, a vascular intervention device delivery system includes a catheter with a proximal end attached to a handle, and a distal carrier segment for mounting a vascular intervention device thereon. The catheter defines a longitudinal axis. A retractable sheath is movable from a first position covering the distal carrier segment to a second position retracted proximally uncovering the distal carrier segment. A pull is attached to the retractable sheath and extends proximally from the retractable sheath toward the handle. A majority of a length of the pull has a cross sectional shape with a concave side that faces the longitudinal axis and is opposite to a convex side that faces away from the longitudinal axis. The cross sectional shape has a width that is greater than a thickness.

In another aspect, a pull for attachment to a retractable sheath of a vascular intervention device delivery system includes a metallic wire with a tapered transition segment positioned between a majority segment and a distal attachment segment. The majority segment has a cross sectional shape with a concave side that is opposite to a convex side, and the cross sectional shape has a width that is greater than a thickness. The concave side and the convex side are flanked by first and second rounded edges. The distal attachment segment has a cross sectional area that is smaller than a cross sectional area of the majority segment.

In still another aspect, a method of using a vascular intervention device delivery system includes maneuvering the distal carrier segment toward a delivery site. The retractable sheath is moved from the first position to the second position at the delivery site by tensioning the pull and moving the pull. The retractable sheath is prevented from prematurely sliding toward the second position during the maneuvering step at least in part by supporting a compression load in the pull. Friction between the pull and the stability sheath is limited at least in part by making a radius of the convex side smaller than an inner radius of the stability sheath.

DETAILED DESCRIPTION

Figure 1:
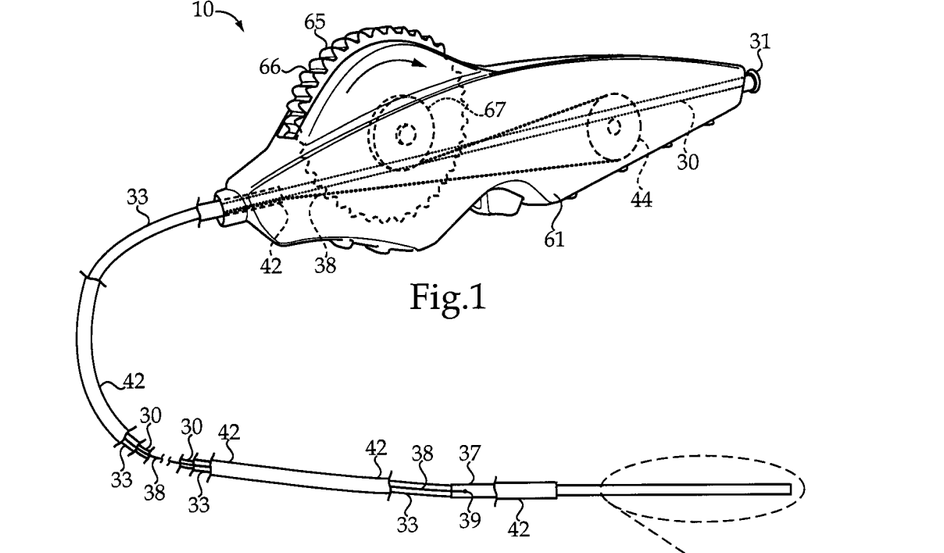
FIG. 1 is a perspective schematic view of a vascular intervention device delivery system according to the present disclosure.
Figure 2:
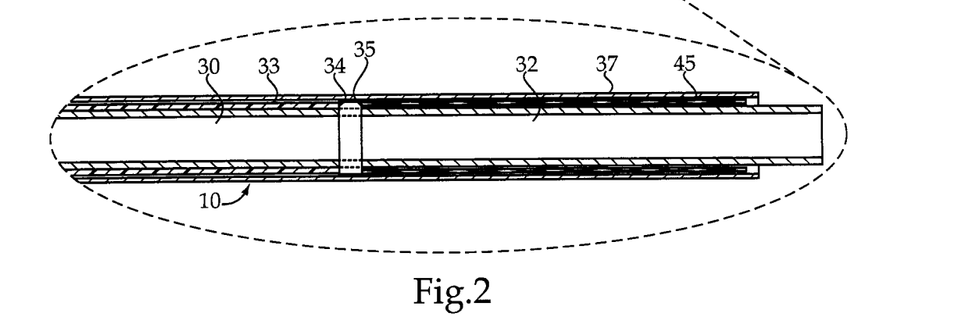
FIG. 2 is an enlarged view of the distal segment of the delivery system shown outlined with a dashed line in FIG. 1.
Figure 3:
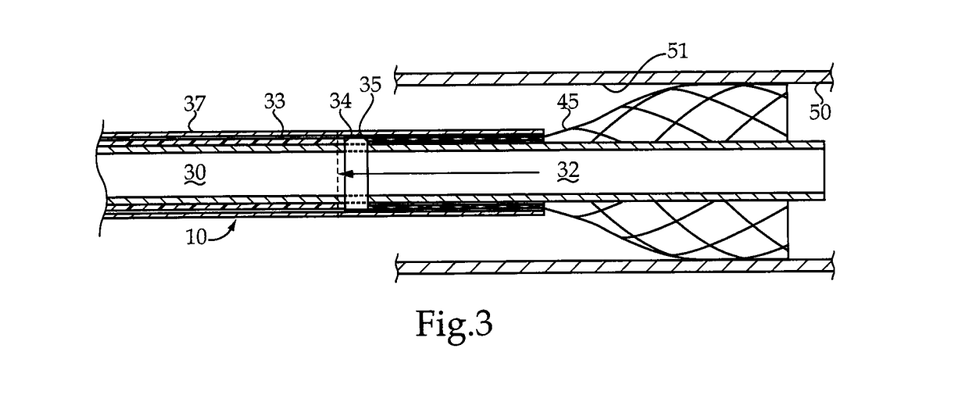
FIG. 3 is a view similar to FIG. 2 about half way through a deployment of a self expanding stent.

Referring initially to FIGS. 1-3, a vascular intervention device delivery system 10 is shown before and during delivery of a self expanding stent 45 into the vessel 50 of a patient. Delivery system 10 includes a handle 61 that may be gripped in one hand by a user during a delivery procedure. Handle 61 may, for instance, be manufactured from a suitable molded plastic, such as in two longitudinal halves that are joined in any suitable manner, such as via a mechanical connection, to form the complete handle 61. A thumbwheel 65 is rotatably mounted in the handle 61 and has a radially outward thumb surface 66 and a spool 67. An inner catheter 30 has a proximal end 31 attached to handle 61, and a distal carrier segment 32 for mounting a vascular intervention device, such as a self expanding stent 45, thereon. Proximal end 31 may take the form a Luer lock fitting to receive a wire guide, or so that treatment fluids or the like may be injected through inner catheter 30 in a manner well known in the art. The Luer lock fitting that comprises the proximal end 31 of inner catheter 30 may be mechanically connected to the handle, such as via an interaction between molded surfaces of the handle halves and the external surface of the Luer lock fitting. A retractable sheath 37 is movable with respect to inner catheter 30 from a first position covering the distal carrier segment 32 to a second position indicated by the dashed line in FIG. 3 at which the retractable sheath 37 has been retracted proximally to uncover the distal carrier segment 32. FIG. 3 shows the retractable sheath 37 about half way between the first position and the second position. Delivery system 10 may include an outer catheter 33 with a distal end 34 that terminates as a pusher band at a proximal end 35 of the distal carrier segment 32 in a manner similar to other stent delivery systems known in the art. The distal end 34 of outer catheter 33 may assist in preventing movement of stent 45 in a proximal direction when retractable sheath 37 is being slid from its first position toward its second position. A proximal end of the outer catheter 33 may be positioned in, and attached to, handle 61.

A pull 38 extends between the spool 67 of thumbwheel 65 and the retractable sheath 37. Pull 38, which preferably is less elastic than the retractable sheath 37, may be attached to retractable sheath 37 at an attachment 39 in any manner known in the art, such as by welding pull 38 to a metallic reinforcement of retractable sheath 37. In some versions of the vascular intervention device delivery system 10 of the present disclosure, pull 38 will be longer than retractable sheath 37. Nevertheless, retractable sheath 37 could be longer than pull 38 without departing from the present disclosure. Pull 38 may comprise a metallic curved cross-section thin band of metal, such as stainless steel.

A wire retention/stability sheath 42 receives and surrounds a majority of the length of pull 38, and serves to keep pull 38 in close proximity to the outer surface of inner catheter 30 over much of the length of delivery system 10. Stability sheath may receive at least a portion of each of the pull 38, the inner catheter 30 and the outer catheter 33, as shown. In the illustrated embodiment, wire retention/stability sheath 42 terminates, and is attached at its proximal end, at a fixation point within handle 61. Nevertheless, other configurations for attachment of wire retention/stability sheath 42 would also fall within the intended scope of this disclosure.

When in its pre-deployment configuration, as shown in FIGS. 1 and 2, a vascular intervention device, such as a self expanding stent 45, is disposed between an outer surface of the distal carrier segment 32 of inner catheter 30, and an inner surface of the retractable sheath 37. During a typical procedure, the distal carrier segment 32 is positioned at a treatment location 51 within a vessel 50 of a patient. After achieving proper positioning, the user then grips handle 61 and begins to rotate thumbwheel 65 so that pull 38 is wound onto spool 67. As this occurs, pull 38 and retractable sheath 37 move proximally with respect to inner catheter 30 to allow the self expanding stent 45 to expand away from carrier segment 32 and into contact with the inner wall of vessel 50 in a manner well known in the art. During this process, inner catheter 30 and outer catheter 33 may be placed in compression while both pull 38 and retractable sheath 37 are in tension. According to the present disclosure, handle 61 and thumbwheel 65 may include a structure that allows thumbwheel 65 to rotate to wind pull 38 onto spool 67, but prevent rotation in an opposite direction. This aspect of the disclosure allows the user to stop the deployment procedure while retaining the stored elastic energy in pull 38 and retractable sheath 37.

Figure 6:
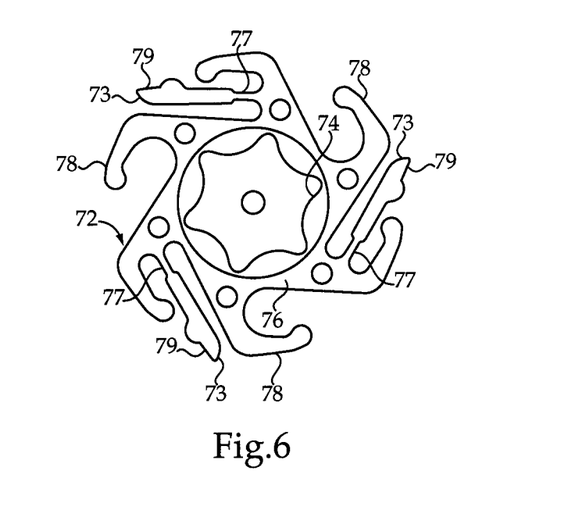
FIG. 6 is a side view of a ratchet pawl for the vascular intervention device delivery system of FIG. 4.
Figure 7:
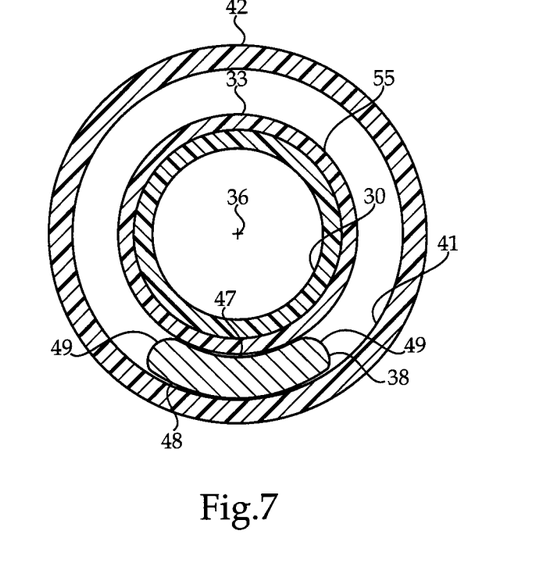
FIG. 7 is a sectioned view through a portion of the vascular intervention device delivery system as viewed along section lines 7-7 of FIG. 5.
Figure 8:
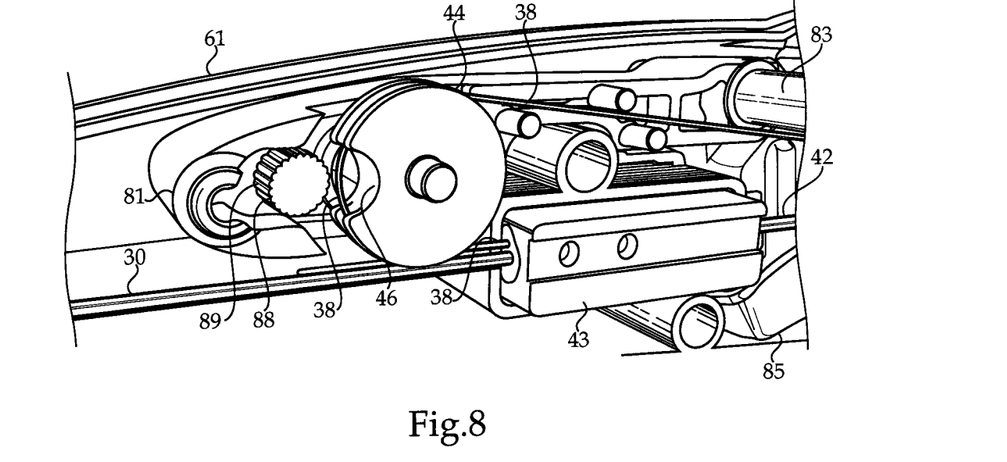
FIG. 8 is a partial perspective view of a portion of the handle from FIG. 4 that includes the idler wheel.
Figure 9:
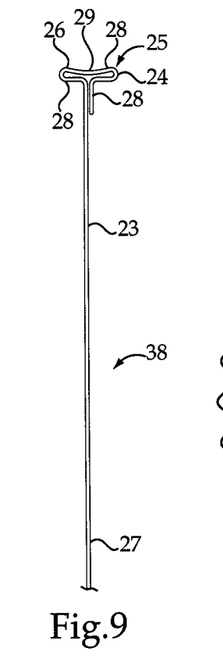
FIG. 9 is a side view of a portion of a pull for the vascular intervention delivery system of the present disclosure.

Referring now in addition to FIGS. 4-14, various features of the vascular intervention device delivery system 10 are shown and discussed. Handle 61 may be formed from a suitable plastic to include a key shaped hub 62 that is received in a matching key shaped opening 74 defined by ratchet pawl 72 of a ratchet 70. This configuration permits assembly of ratchet pawl 72 to key shaped hub 62 in a plurality of different but equivalent angular orientations. Key shaped hub 72 may define a central opening that receives an axle 63 to define an axis 64 about which thumbwheel 65 rotates. Thumbwheel 65 includes a radially outward thumb surface 66 and a radially inward ratchet surface 71 of the ratchet 70. Thumbwheel 65 may also include a spool 67 upon which the pull 38 is wound when the device delivery system 10 is operated. In this version, the wire retention/stability sheath 42 terminates at a junction box 43 (not shown in FIG. 4 for the sake of clarity) positioned within handle 61. As in the previous version, the pull 38 is positioned within the wire retention/stability sheath 42 and emerges from the junction box 43 to wrap around an idler wheel 44 and return in a reverse direction for being wound onto spool 67 as best shown in FIGS. 7 and 8. Idler wheel 44 is rotatably mounted in handle 61 and positioned proximal to thumbwheel 65. Ratchet 70 prevents thumbwheel 65 from rotating in a forward direction, but the retractable sheath 37 (FIGS. 1-3) moves responsive to rotation of thumbwheel 65 in a reverse direction.

Ratchet pawl 72 of ratchet 70 includes a catch 73 that takes the form of spiral arms 79 that are attached to a central body 76 by living hinges 77. Ratchet pawl 72 may most conveniently be formed of a suitable plastic material. When thumbwheel 65 is rotated in a reverse direction, each of the three catches 73 will click and be received into respective stops 75 that define ratchet surface 71. In this embodiment, ratchet catches 73 are equally distributed 120° apart around the axis 64 defined by axle 63. Thus, the three catches 73 will simultaneously contact the ratchet surface 71 at three different locations located 120° apart about axis 64. Those skilled in the art will appreciate that a ratchet pawl 72 having two, four or more catches 73 would also fall within the intended scope of this disclosure.

Figure 4:
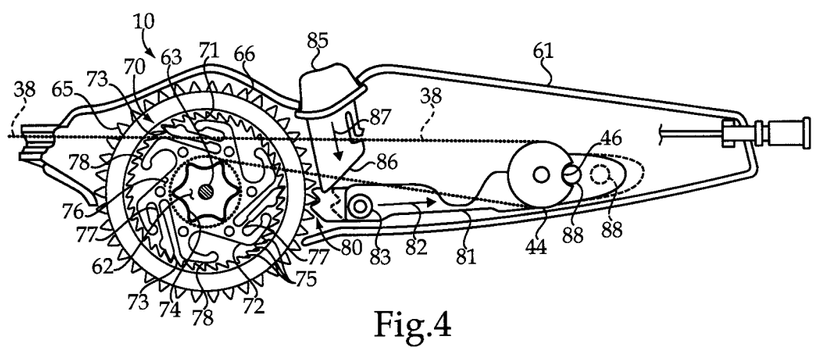
FIG. 4 is a sectioned side view of a handle portion of a vascular intervention device delivery system according to the present disclosure.
Figure 5:
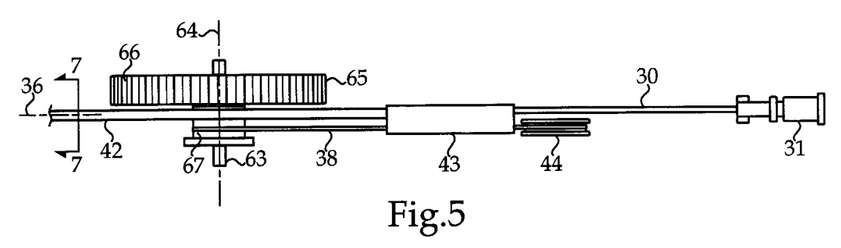
FIG. 5 is a top view of the inner workings of the vascular intervention device delivery system of FIG. 4, minus the handle.

As best shown in FIGS. 4 and 6, the ratchet pawl 72 includes curved arms 78 that are distributed to provide a circular guide for the thumbwheel as the ratchet teeth rotate around the fixed ratchet. Thus, in some embodiments, the use of curved arms 78 could permit omission of axle 63 as shown, since the thumbwheel would rotate about axis 64 with the curved arms 78 contacting ratchet surface 71, even without the inclusion of axle 63. It is also worth noting that both the ratchet pawl 72 and the ratchet surface 71 of thumbwheel 65 may be made out of plastic. By making both the pawl 72 and the ratchet surface 71 from the same material, the potential creation of the debris caused by the interaction of metal with plastic can be avoided.

In addition to ratchet 70, vascular intervention device delivery system 10 may include a lock 80 that allows thumbwheel 65 to be disabled during shipment and during positioning of the distal carrier segment 32 (FIGS. 1-3) at a delivery site 51 within a patient. The lock 80 is movable between a locked position, as shown in FIG. 4, and an unlocked position shown in FIG. 8 and by dashed lines in FIG. 4. The lock 80 includes a latch 81 positioned in handle 61 and movable along a line 82 between the locked position at which the latch 81 engages and contacts the radially outward thumb surface 66 of thumbwheel 65, and the unlocked position at which the latch 81 is out of contact with the radially outward thumb surface 66. Lock 80 also includes a pusher 85 that is at least partially positioned outside of handle 61, but on an opposite side of handle 61 from the exposed portion of thumbwheel 65. The pusher may include a wedge 86 that engages a post 83 of latch 81. Post 83 may be oriented perpendicular to the line 82 of action of latch 81. Vascular intervention device delivery system may be enabled by depressing pusher 85 along line 87 to move latch 81 out of contact with radially outward thumb surface 66 of thumbwheel 65.

Latch 81 not only moves between positions in contact and out of contact with thumbwheel 65, movement of lock 80 may also enable rotation of idler wheel 44. In particular, idler wheel 44 may define a perimeter notch 46. A pin 88 is mounted to move with latch 81 between a position in which pin 88 is received in perimeter notch 46 to block rotation of idler wheel 44, (FIG. 4) and a second position (FIG. 8) outside of perimeter notch 46 to permit rotation of idler wheel 44. Pin 88 may include a knurled surface 89 that is in contact with pull 38 when pin 88 is in the first position received in perimeter notch 46. The knurled surface 89 is out of contact with pull 38 in the second position as best shown in FIG. 8. Although pin 88 is shown as attached to a moving with latch 81, pin 88 could be mounted to move independently of latch 81 without departing from the intended scope of the present disclosure. When pin 88 is in the first position received in perimeter notch 46 and has its knurled surface 89 in contact with pull 38 as shown in FIG. 4, this interaction not only serves to prevent rotation of idler wheel 44, but also serves to provide columnar support for pull 38 to support against movement of retractable sheath 37 when the device is being maneuvered to a delivery site 51 within a patient. For instance, friction on retractable sheath 37 in the proximal direction during the maneuvering procedure is inhibited by the columnar strength provided by pull 38 and its contact with pin 88. Those skilled in the art might appreciate that the knurled surface 89 may help, but it is mostly believed to be the pressured applied by pin 88 onto the pull 38 that provides the columnar support when the two features are in contact. Other potential options in place of knurled surface 89 include but are not limited to a rubber overmold on pin 88 to create friction on pull 38, or pin 88 could have a splined surface or maybe even a rough/smooth finish without departing from the present disclosure.

Figure 13:
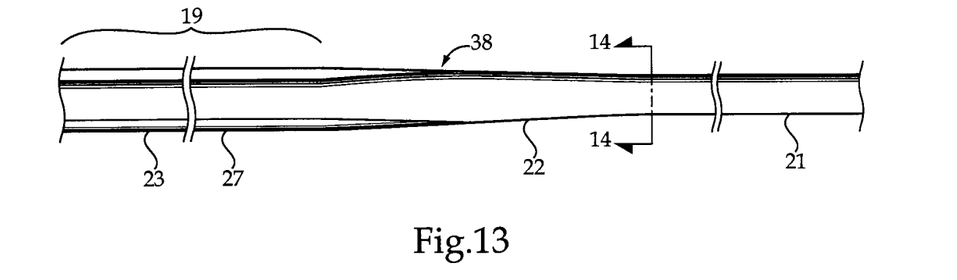
FIG. 13 is a top view of a pull according to the present disclosure.
Figure 14:
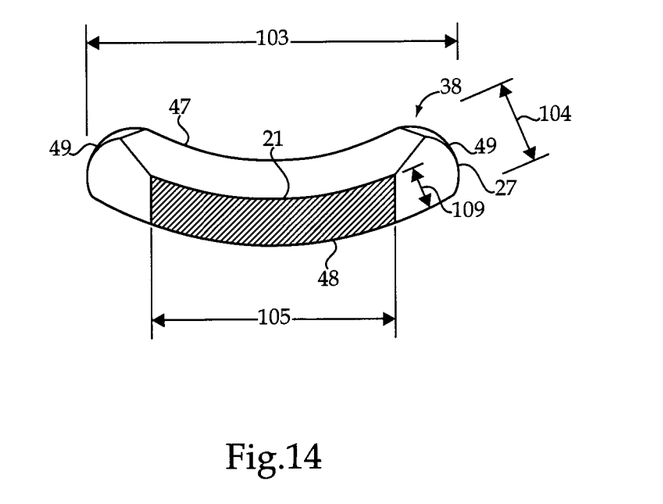
FIG. 14 is a sectioned view through the pull of FIG. 13 as viewed along section line 14-14.

Referring now specifically to FIGS. 9-14, Pull 38 may be manufactured from a single length of spring stainless steel having the cross sectional shape best shown in FIG. 14. After being cut to length, some material may be removed to form a distal attachment segment 21 that is separated from a majority segment 19 by a tapered transition segment 22. This removal of material may be accomplished by, for instance, a punch and dye process, or by some machining process such as electrical discharge machining in a manner well known in the art. As best shown in FIG. 14, the distal attachment segment 21 may have a cross sectional area that is smaller than a cross sectional area of the majority segment 19. The majority segment 19 may have a width 103 that is greater than a thickness 104. Likewise, the distal attachment segment 21 may have a width 105 that is greater than a thickness 109. Those skilled in the art will appreciate that majority segment 19 constitutes a majority of the length of pull 38. Thus, distal attachment segment 21 inherently constitutes a minority of the length of pull 38. As best shown in FIG. 14, the distal attachment segment 21 is flatter than the majority segment 19, in order to better facilitate attachment to retractable sheath 37. In the present example embodiment, "flatter" means that distal attachment segment 21 occupies a smaller arc of a circle than the arc of the circle associated with the majority segment.

Figures 11, 12:
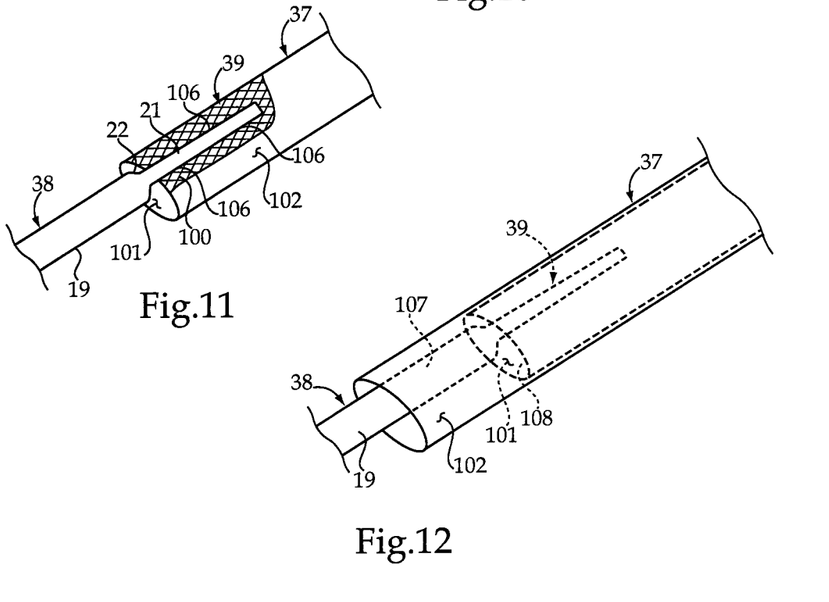
FIG. 11 is a perspective schematic view of an attachment region of the pull to the retractable sheath according to one aspect of the present disclosure.
FIG. 12 is a perspective schematic view of the attachment region of a pull to the retractable sheath according to another aspect of the present disclosure.

After pull 38 is machined or formed into the shape shown in FIGS. 13 and 14, the distal attachment segment 21 may be attached to retractable sheath 37 in a number of ways. For instance, retractable sheath 37 may start out as a conventional metallic braid 100 that is welded to distal attachment segment 21 at one or more weld locations 106. This construction keeps braid 100 and distal attachment segment 21 of pull 38 in place for sliding over a inner tube 101, which may be formed of a low friction polytetrafluoroethylene (PTFE). Then, an outer tube 102 of a suitable polymer cover is created so that the braid 100 and the distal attachment segment 21 of pull 38 are laminated between the PTFE inner tube 101 and the polymer outer tube 102. FIG. 11 shows an attachment structure that may be suitable for shorter stents, such as those that may range from 40-120 millimeters in length. For longer stents, an attachment configuration like that shown in FIG. 12 may be substituted in place. In this version, the attachment is much the same as that of FIG. 11, except that the outer polymer cover tube 102 covers a segment 107 of pull 38 that is proximal to a proximal end 108 of the PTFE tube 101, which terminates at a location similar to that shown in FIG. 11. Although the distal attachment segment 21 is welded to the braid of retractable sheath 37, it is believed that much of the attachment load is carried by being laminated with braid 100 between the inner PTFE tube 101 and the outer polymer cover tube 102. Thus, in the illustrated embodiment, retractable sheath 37 includes the inner PTFE tube 101, the braid or reinforcement 100 and the outer polymer cover 102. While the distal carrier segment 32 is being maneuvered to the delivery site 51, friction on the outer surface of retractable sheath 37 that might otherwise prematurely slide it toward its second position, is prevented at least in part by supporting a compression load in pull 38. The curved cross section of pull 38 helps to prevent pull 38 from buckling under this compression load, and the contact with pin 88 facilitates transfer of this compression load from the pull 38 to pin 88 and hence to handle 61 during the maneuvering step.

Referring specifically to FIGS. 7 and 8, pull 38 may have a curved cross section with a concave side 47 that is opposite to a convex side 48, both of which are flanked by rounded edges 49. A rounded edge according to the present disclosure includes a pair of radiused corners separated by a planar portion. The concave side 47 and the convex side 48 are the long sides of the pull 38 cross section. The concave side 47 faces longitudinal axis 36, and the convex side 48 faces away from longitudinal axis 36. In the illustrated embodiment, the idler wheel 44 and the spool 67 are arranged so that the convex side 48 is in contact with idler wheel 48, and the concave side 47 is in contact with spool 67. Nevertheless, those skilled in the art will appreciate that the opposite configuration would also fall within the scope of the present disclosure. Pull 38 may be positioned between stability sheath 42 and outer catheter 33. As best shown in FIG. 7, the convex side 48 of pull 38 is in contact with the inner surface 41 of stability sheath 42. The convex side 47 may be in contact with, or adjacent to, the outer surface 55 of outer catheter 33. In order to reduce friction, and reduce the contact area between pull 38 and stability sheath 42 as well as outer catheter 33, the radius of convex side 48 may be smaller than the radius of the inner surface 41 of stability sheath 42. Likewise, the radius of concave side 47 may be less than the outer radius 55 of outer catheter 33. Pull 38 may be manufactured from a suitable band of spring stainless steel to have the curved cross sectional shape shown in FIG. 7 (and FIG. 14). Pull 38 may be made from stainless steel with a sufficiently large cross section that the pull does not stretch when in tension at expected magnitudes (tens of Newtons) during a delivery process. The curved cross sectional shape of pull 38 may provide columnar support to retractable sheath 37 when in compression while the distal carrier segment 32 is being maneuvered to delivery site 51.

Referring now more specifically to FIGS. 9 and 10, pull 38 is again shown in the form of a relatively thin band of spring steel with a curved cross section. Preferably, pull 38 is one integral length from its distal attachment point 39 to a proximal end 24 that is connected to spool 37. Pull 38 may have a majority of its length biased toward a straight configuration. In order to form proximal end 24 with an integral anchor 25, a proximal segment 23 of pull 38 may be annealed to provide greater ductility than a distal segment 27, which may comprise a majority of the length of pull 38. As used in the present disclosure, the term "integral" means that the identified features originate from the same part. Thus, integral anchor 25 is merely a deformed segment of the pull 38 and was never detached therefrom. An integral anchor 25 according to the present disclosure has never been separated from a remaining portion of pull 38, and then attached by some means such as a weld or adhesives or the like. Although integral anchor 25 could be formed on an un-annealed proximal segment 23 of pull 38, there are at least two reasons to consider annealing proximal segment 23 in order to increase ductility relative to the distal segment 27. First, forming un-annealed spring steel into the profile shape (T-shape) 26 can potentially result in breakage or substantial cracking at the severe bends where the wire band is bent back upon itself. Secondly, the best results have been observed when the vascular intervention device delivery system 10 is initially manufactured, stored prior to use, and during an initial use maneuvering to the desired implantation site by having the pull 38 wound at least one time and maybe as many as three to four times around the collection surface 90 of spool 67. In other words, proximal segment 23 may be wound at least once completely around collection surface 90 when the retractable sheath is at its first position covering the self expanding stent 45. The greater ductility of the proximal section 23 not only helps in the forming of the integral anchor 25 without cracking or breakage, but also better facilitates the initial winding of pull 38 onto spool 67.

Figure 10:
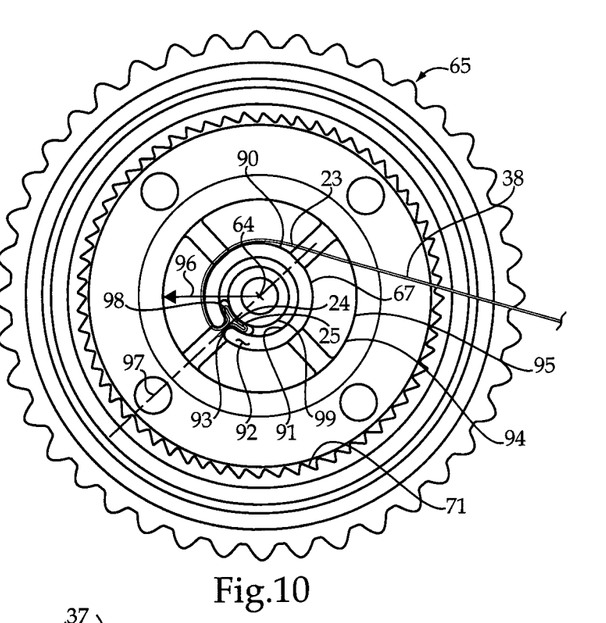
FIG. 10 is a side view of the pull of FIG. 9 partially wound onto a spool for the thumbwheel of FIG. 4.

In the illustrated example, the integral anchor 25 has a T-shape 26 in which each of three legs 28 of the T-shape 26 is defined by two side by side segments of the pull 38. The top 29 of the T-shape 26 may be concave to match an outer radius of axle hub outer surface 99. The spool 67 defines a T-shaped slot 98 that is sized to received the T-shape 26 of the integral anchor 25. T-shaped slot 98, which may also include a top concave shape, opens in a direction parallel to axis 64. After passing through the T-shaped slot 98, the integral anchor 25 is positioned to extend through an opening 93 in a wall 92 that separates an inner surface 91 from collection surface 90 of spool 67. Thus, the integral anchor 25 will contact the inner surface 91, and extend through the opening 93, which may have a centerline 97 that intersects axis 64.

Spool 67 may include a rim 94 in order to help inhibit wound segments of pull 38 from sliding off of collection surface 90. Rim 94 includes an outer rim surface 95 that is a rim radius 96 from axis 64. The portion of pull 38 that is wound around collection surface 90 may be less that the rim radius 96 from axis 64. Collection surface 90 may have a width that is about twice a width of pull 38. The term about twice means that the ratio of widths is two when rounded to one significant digit. This aspect of the disclosure helps to inhibit slippage in pull 38 that could result from a less tight winding of pull 38 around spool 67. Preferably, pull 38 is contact wound around collection surface 90. As used in the present disclosure, the term "contact wound" means that each winding of the pull 38 is either in contact with collection surface 90 or in contact with a previous winding of pull 38 around contact surface 90. Although the illustrated embodiment shows the proximal end 24 of pull 38 terminating in a T-shaped 26 integral anchor 25, those skilled in the art will appreciate that other integral anchor shapes could be utilized without departing from the present disclosure. For instance, an integral anchor according to the present disclosure may include bends in the pull 38 that result in enlarged portions extending above and below a thickness profile of pull 38. In the illustrated example, the two top legs 28 of the T-shape 26 meet this requirement. However, those skilled in the art will appreciate that numerous other integral anchor shapes, including asymmetrical shapes, would also fall within the intended scope of the present disclosure. Some of these alternatives might require a different shaped slot from T-shaped slot 98 or may require no slot. Provided that the anchor is integral, these other alternatives as would occur to persons with ordinary skill would also fall within the intended scope of this disclosure. Thus, other alternative anchor shapes could fit in the annular space between the inner surface 91 and the axle hub outer surface 99.

In the illustrated embodiment, one might anneal a proximal segment 23 on the order of 30-40 millimeters in length, and form the integral anchor 25 out of maybe 10-15 millimeters of that proximal segment 23. The remaining portion of the proximal segment 23, and maybe some of the distal segment 27 may be wound onto spool 67 at the time of assembly and manufacture when retractable sheath 37 is still at its distal first position. By manufacturing with the expectation that at least one and maybe as many as three or four windings will begin on spool 67 when retractable sheath 67 is still in its first position, tight tolerances on a precise length for pull 38 are not necessary. Furthermore, tight tolerances with regard to what length of the pull 38 is consumed in order to form integral anchor 25 are also relaxed because of the initial windings on spool 67. This relaxation of dimensional length tolerances with regard to pull 38 not only reduces potential scrap, but also provides for a more robust design that arrives ready for use with little to no slack in pull 38 when the deployment procedure begins.

INDUSTRIAL APPLICABILITY

The present disclosure is generally applicable to vascular intervention device delivery systems, and more particularly to a delivery system for delivery of self expanding stents and other vascular intervention devices with self expanding action. The present disclosure finds specific applicability to delivery of relatively long vascular intervention devices that produce substantial friction on the inner surface of retractable sheath 37, and thus require higher forces on retractable sheath 37 and pull 38 in order to successfully deliver the vascular intervention device to an intended treatment site.

The vascular intervention device delivery system 10 will typically be packaged in a conventional sterile packaging in a known manner for shipment. After a wire guide (not shown) has been positioned in a patient's body across a treatment location 51, the inner catheter 30 may be slid over the wire guide to position the distal carrier segment 32 and the attached self expanding stent 45 at the delivery site 51 within the vessel 50 of the patient. Thereafter, the wire guide may be withdrawn or left in place. During this portion of the procedure, the thumbwheel 65 of the vascular intervention device delivery system 10 may be disabled by maintaining the lock 80 in its locked position as shown in FIG. 4. It is also important to note that when the vascular intervention device delivery system 10 is being maneuvered to a delivery site 51 (FIG. 3) the pin 88 is received in perimeter notch 46 of idler wheel 44 to prevent idler wheel 44 from rotating and to place the knurled surface 89 of pin 88 in contact with pull 38 to inhibit movement of retractable sheath 37 toward the proximal direction to uncover stent 45. The curved cross section of pull 38 may provide columnar support to prevent premature sliding movement of retractable sheath 37. The compression load may be transferred to handle 61 via pin 88.

After the distal carrier segment 32 has arrived at and is properly positioned at delivery site 51, and it is now time to deploy the self expanding stent 45, the user may depress pusher 85 to disengage lock 80 and move latch 81 out of contact with the radially outward thumb surface 66 of thumbwheel 65. This movement of lock 80 also moves pin 88 out of perimeter notch 46 and out of contact with pull 38 as best shown in FIG. 8. This movement enables rotation of idler wheel 44. In addition, when pin 88 is moved out of contact with pull 38, the columnar support of pull 38 is relieved, and readies pull 38 to support tension as thumbwheel 65 is rotated to take up the pull 38 on spool 67.

A method of operating vascular intervention device delivery system 10 includes rotating the thumbwheel 65 in a reverse direction to wind pull 38 onto spool 67 to build up tension in the retractable sheath 37 and pull 38 without moving the retractable sheath 37 relative to the distal carrier segment 32 of inner catheter 30. The "reverse direction" is clockwise in the view of FIG. 1 and counterclockwise in the view of FIG. 4. In both cases, the "reverse direction" means that the user's thumb moves toward their palm to rotate the thumbwheel 65. Next, a portion, which is less than all, of the distal carrier segment 32 may be uncovered by continuing to rotate the thumbwheel 65 in the reverse direction. During this portion of the procedure, friction between the pull 38 and the stability sheath 42 is limited at least in part by making a radius of the convex side 48 smaller than the inner radius 41 of stability sheath 42 as best shown in FIG. 7. Friction is limited by reducing the contact area between the two components. In addition, friction may also be limited by making a radius of the concave side 47 of pull 38 smaller than an outer radius 55 of outer catheter 33.

By forming pull 38 to have a relatively thin curved cross section, more material is available in the cross sectional shape so that the length of the pull 38 remains constant at tension levels (tens of Newtons), sufficient to move the retractable sheath 37 for its first position to its second position. Thus, while maneuvering to the delivery site, the pull 38 may be placed in compression to support a compression load, and during the delivery procedure the pull 38 is placed in tension to support delivery of the stent 45 to the delivery site 51. At some point during the delivery procedure, the user may then pause rotation of the thumbwheel 65 in the reverse direction. For instance, the user may pause in order to confirm that the vascular intervention device, such as a self expanding stent 45, is being delivered to the desired location in the vessel 50 of the patient. While the rotation of the thumbwheel 65 is paused, tension in the pull 38 and the retractable sheath 37 is maintained by holding the ratchet 70 and preventing rotation of the thumbwheel 65 in the forward direction. Ratchet 70 may be considered to be in a hold configuration when catches 73 are received in one of the stops 75 of the ratchet surface 71. A remaining portion of the distal carrier segment 32 is then uncovered to facilitate complete deployment of the self expanding stent 45 by resuming rotation of the thumbwheel 65 in the reverse direction until retractable sheath 37 arrives at its second position fully uncovering distal carrier segment 32.

An important aspect of the ratchet operated vascular intervention device delivery system 10 of the present disclosure may be to allow for rotation of thumbwheel 65 in one direction only. This means that the pull 38 and hence the retractable sheath 37 can only be pulled proximally. If the thumbwheel 65 were able to rotate in both directions, it could cause the pull 38 to slack and possibly jump out of the collection diameter of the spool 67 on thumbwheel 65. Also, by keeping the rotation of thumbwheel 65 to one direction only, ratchet 70 allows all of the energy already placed in the system 10 by the user to be maintained. For example, if the user was to partially deploy a self expanding stent 45 that had a deployment force of 30N the user will have to put effort into getting the stent to partially deploy. This effort could have caused the sheath 37 to stretch slightly and also the inner catheter 30 and outer catheter 33 to compress slightly. If this energy were lost when the thumbwheel 65 were released, it would mean that when the deployment was resumed from that point, the user would have to rotate the thumbwheel 65 an amount in order to reestablish tension in the system 10 again before the self expanding stent 45 would continue to deploy. This may be especially important in the case of deploying longer stents that require higher forces.

Apart from providing column strength to avoid premature deployment of the stent while the device is maneuvered to a delivery site, the curved pull of the present disclosure also reduces a second risk associated with circular cross section retraction wire pulls. In particular, in some instances, round wires can become wrapped around the inner catheter, such as during assembly. If the round pull wire became wrapped around the inner catheter, this phenomenon can increase the deployment force, result in a failure to deploy or a failure due to partial deployment. This may happen because the wire wrapped around the inner catheter could be pulled down onto the inner catheter and get jammed. This risk of wire wrapping can be further increased when the retraction wire design requires multiple round wires. Because the curved wire of the present disclosure has the capacity to fill a larger volume of space within the delivery system, there is less likelihood that the wire can become twisted or wrapped around the inner catheter, thus reducing the risks associated with circular cross section pull wires. By forming the pull wire 38 to have curved cross section with a smaller and flatter cross section at its distal attachment segment, the smaller cross section reduces the profile in the attachment region to further reduce deployment friction in the system.

It should be understood that the above description is intended for illustrative purposes only, and is not intended to limit the scope of the present disclosure in any way. For example, although the present disclosure is illustrated in the context of a thumb wheel actuated delivery system, those skilled in the art will appreciate that the pull of the present disclosure could find equal application in other delivery systems, such as pin and pull systems known in the art without departing from the present disclosure. Thus, those skilled in the art will appreciate that other aspects of the disclosure can be obtained from a study of the drawings, the disclosure and the appended claims.

What is claimed is:

1. A vascular intervention device delivery system comprising:
   a handle;
   a catheter with a proximal end attached to the handle, and a distal carrier segment for mounting a vascular intervention device thereon, and defining a longitudinal axis;
   a retractable sheath has a proximal end positioned outside of the handle and being movable from a first position covering the distal carrier segment to a second position retracted proximally uncovering the distal carrier segment;
   a stability sheath attached to the handle and extending toward the distal carrier segment, and the proximal end of the retractable sheath being received in the stability sheath in both of the first and second positions;
   a pull attached to the retractable sheath and extending proximally from the retractable sheath toward the handle, and a majority of a length of the pull having a cross sectional shape with a concave side that faces the longitudinal axis and is opposite to a convex side that faces away from the longitudinal axis; and
   the cross sectional shape has a width that is greater than a thickness;
   wherein the pull includes a distal attachment segment that is a minority of the length, and has a cross sectional area that is smaller than a cross sectional area of the cross sectional shape of the majority of the length of the pull; and
   the distal attachment segment is attached to a metallic reinforcement of the retractable sheath at a location outside of, and away from, the handle.

2. The vascular intervention device delivery system of claim 1 wherein the distal attachment segment has a concave side that is flatter than a concave side of the majority of the length of the pull.

3. The vascular intervention device delivery system of claim 1 wherein the distal attachment segment has a width that is smaller than a width of the majority of the length of the pull.

4. The vascular intervention device delivery system of claim 1 wherein the pull includes a tapered transition segment between the majority of the length and the distal attachment segment.

* * * * *